Aug. 5, 1941. P. H. ROLAND Plant Pat. 480
ROSE PLANT
Filed Sept. 21, 1940
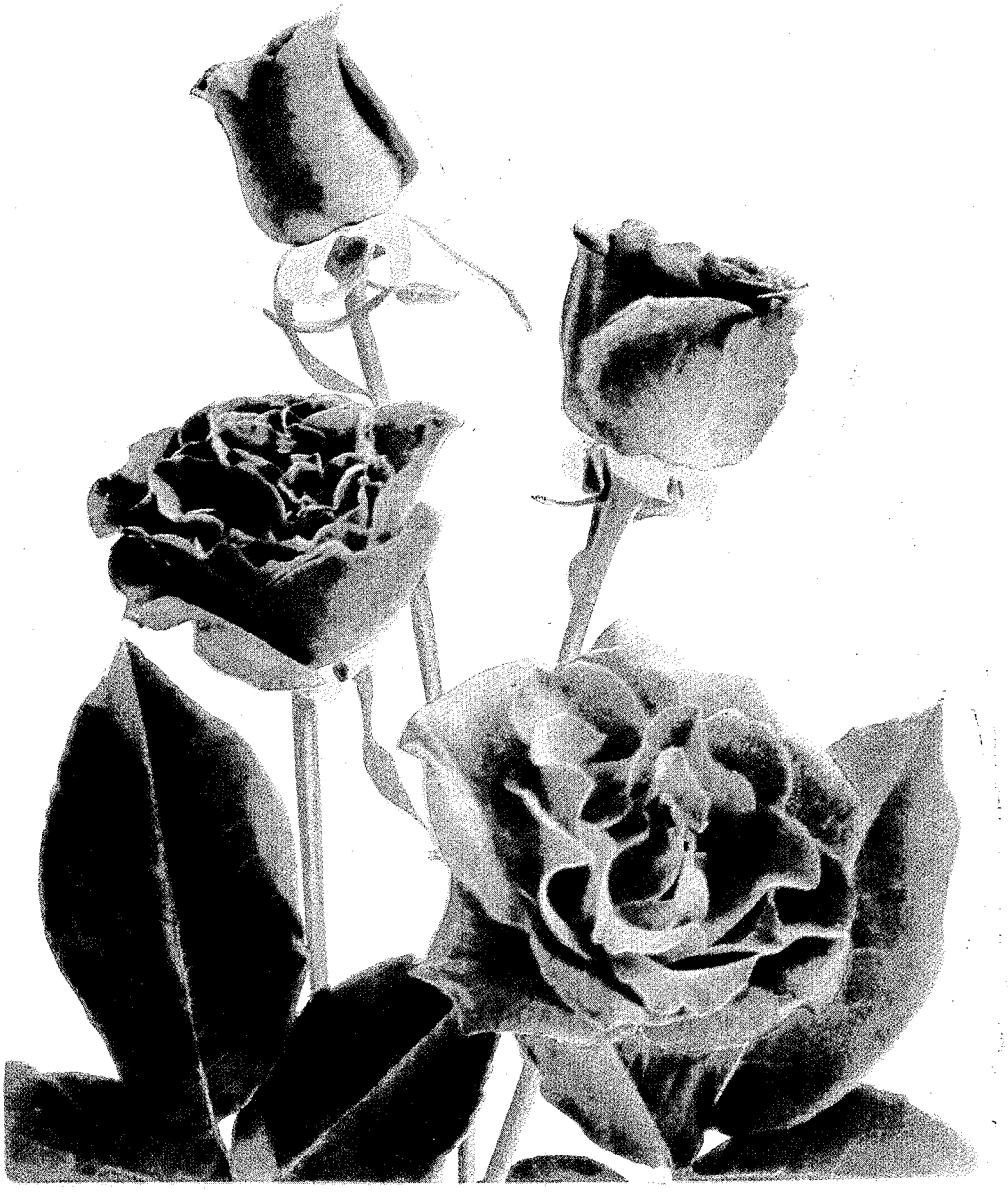
Inventor
Phillips H. Roland
By Robbins & Robbins
Attorneys Patented Aug. 5, 1941

Plant Pat. 480

UNITED STATES PATENT OFFICE

480

ROSE PLANT

Phillips H. Roland, Nahant, Mass., assignor to Thomas Roland, Inc., Nahant, Mass., a corporation of Massachusetts Application September 21, 1940, Serial No. 357,798

1 Claim. (Cl. 47—61)

This discovery relates to a new and distinct variety of hybrid tea rose plant, originating as a sport of a true Talisman plant in my possession and immediately recognized by me as of commercial value primarily because of the unusual and attractive coloring of the bloom.

It is to be noted at the outstart that so far as foliage and growth of the plant are concerned, there appears to be no difference whatever, and the following detail description is therefore more or less general since the Talisman variety is well known.

However, as regards the flower, this new variety possesses a more distinct and clear red color than any of the known Talisman sports. This color moreover is difficult to define as there does not appear to be any corresponding color in the standard or most commonly used color charts. For this reason, general or dictionary color terminology is herein employed. To this end, as the buds begin to open, the color appears carmine reverse with a scarlet-red color on the face of the petals. When the flower is fully open, the orange in the red appears to have faded considerably and leaves the color characteristic of the bloom scarlet-crimson, as nearly as I can define the combination where there exists so much orange in the red.

Type: Tender; bush; sport; for cut flowers and garden decoration.
Class: Hybrid tea.
Propagation: It holds its distinguishing characteristics through succeeding propagations by cuttings, grafting, budding, and layering.

*Flower*

Locality where grown: Revere, Massachusetts.
Flowers borne: Singly on strong long stems.
Quantity of bloom: Free in greenhouse.
Continuity: Continuous.
Fragrance: Strong; tea.
Bud:

*Peduncle.*—Medium length; medium heavy; green; medium erect; almost smooth; few green brown prickles.

*Before calyx breaks.*—*Size*—medium. *Form*—short; pointed with a conspicuous neck with foliaceous appendages on the surface of the bud with slender foliaceous parts extending beyond the tip of the bud equal to ¾ of its length.

*As first petal opens.*—*Size*—medium. *Form*—ovoid. *Color:* outside—Carmine; inside—Scarlet-Red (no equivalent chart color). *Opening*—opens up well.

Bloom:

*Size, when fully open.*—Medium, 4 inches to 5 inches.

*Petalage.*—Double (two or even three rows), but the stamens not hidden; from 24 to 30 petals arranged regularly.

*Form.*—Cupped; petals remaining at first loosely cupped; becoming later, at maturity, loosely cupped outward.

Petals: Thick; leathery with inside velvety and outside shiny.

*Shape.*—Outside—oval, intermediate—oval; scalloped with two notches. Inside—obovate; irregular.

*Color.*—Shaded, washed.

This description of a newly opened flower was made from a rose grown in a greenhouse in May, 1940, at Revere, Massachusetts:

*Color:* When the flower opens fully the orange in the red appears faded giving it the appearance of a combination of scarlet and crimson.

This description was made from a rose that was open for three days, indoors, in May, 1940:

*Unchanged*

*Behavior.*—Persist.

*Flower longevity.*—Cut roses grown in greenhouse kept at living room temperatures, 6–7 days in May.

*Reproductive organs*

Stamens: Many; mixed with petaloids.
Filaments: Short; reddish; few with anthers.
Anthers: Yellow; all open at once.
Pollen: Moderate.
Pistils: Many.
Styles: Uneven; medium heavy; bunched.
Stigma: Yellow.
Ovaries: Some protruding from calyx.
Sepals: Permanent; moderately long; spear-shaped.

*Plant*

Foliage:

*Leaves.*—Compound of 3–5–7; medium size; leathery; glossy.

*Leaflets.*—Ovoid, with apex mucronate; base round, irregularly serrate.

*Color.*—Upper surface—green. Under surface—normal; green.

*Rachis.*—Medium heavy. Upper side—hairy. Under side—moderately thorny.

*Stipules.*—Medium length; medium width; with long points, turning out at an angle less than 45°.

*Disease.*—Resistant to mildew and blackspot.

Growth:

*Habit.*—Upright.

*Growth.*—Vigorous.

*Canes.*—Medium heavy.

*Main stems.*—Green. *Thorns*—many; medium long, straight, with broad base. *Prickles*—several; green. *Hairs*—None.

*Branches.*—Green. *Thorns*—many; medium long, straight; broad base. *Prickles*—several; green. *Hairs*—none.

*New shoots.*—Brown. *Thorns*—many; medium long, with broad base. *Prickles*—many; brown. *Hairs*—none.

I claim:

A new and distinct variety of hybrid tea rose plant, characterized as to novelty by its similarity to the Talisman rose except as to the blossom, and as to the blossom by its unusual color combinations in the bud and full blown stages, substantially as shown and described.

PHILLIPS H. ROLAND.